(12) United States Patent
Paul et al.

(10) Patent No.: US 9,028,538 B2
(45) Date of Patent: *May 12, 2015

(54) VERTEBRAL BODY NERVE AND VEIN CAUTERIZING SYSTEM AND METHOD

(75) Inventors: David C. Paul, Phoenixville, PA (US); Sean Suh, Plymouth Meeting, PA (US); Mark Weiman, Coatesville, PA (US); Jody L. Seifert, Birdsboro, PA (US)

(73) Assignee: Globus Medical, Inc., Audubon, PA (US)

( * ) Notice: Subject to any disclaimer, the term of this patent is extended or adjusted under 35 U.S.C. 154(b) by 137 days.

This patent is subject to a terminal disclaimer.

(21) Appl. No.: 13/608,229

(22) Filed: Sep. 10, 2012

(65) Prior Publication Data

US 2013/0006256 A1  Jan. 3, 2013

Related U.S. Application Data

(63) Continuation of application No. 12/605,836, filed on Oct. 26, 2009, now Pat. No. 8,282,628.

(51) Int. Cl.
| | |
|---|---|
| *A61B 18/08* | (2006.01) |
| *A61B 17/88* | (2006.01) |
| *A61B 18/04* | (2006.01) |
| *A61B 18/14* | (2006.01) |
| *A61F 2/44* | (2006.01) |
| *A61B 17/16* | (2006.01) |
| *A61B 18/02* | (2006.01) |
| *A61B 18/00* | (2006.01) |

(52) U.S. Cl.
CPC ............ *A61B 17/8855* (2013.01); *A61B 18/08* (2013.01); *A61B 18/04* (2013.01); *A61B 18/14* (2013.01); *A61F 2/44* (2013.01); *A61B 17/1671* (2013.01); *A61B 17/8805* (2013.01); *A61B 18/02* (2013.01); *A61B 2018/0022* (2013.01); *A61B 2018/00565* (2013.01); *A61B 2018/00595* (2013.01)

(58) Field of Classification Search
USPC .......................................... 606/92
See application file for complete search history.

(56) References Cited

U.S. PATENT DOCUMENTS

| | | | | |
|---|---|---|---|---|
| 4,709,698 | A * | 12/1987 | Johnston et al. | 606/41 |
| 4,799,479 | A * | 1/1989 | Spears | 606/28 |
| 5,277,201 | A * | 1/1994 | Stern | 607/98 |
| 5,779,698 | A * | 7/1998 | Clayman et al. | 606/39 |
| 5,879,347 | A * | 3/1999 | Saadat | 606/28 |
| 6,425,877 | B1 * | 7/2002 | Edwards | 604/21 |
| 6,602,252 | B2 * | 8/2003 | Mollenauer | 606/46 |
| 6,813,520 | B2 * | 11/2004 | Truckai et al. | 607/101 |
| 7,041,100 | B2 * | 5/2006 | Kreindel | 606/41 |
| 7,179,254 | B2 * | 2/2007 | Pendekanti et al. | 606/28 |
| 7,569,626 | B2 * | 8/2009 | Truckai | 523/218 |
| 8,282,628 | B2 * | 10/2012 | Paul et al. | 606/2 |
| 8,568,420 | B2 * | 10/2013 | O'Halloran et al. | 606/93 |
| 2003/0105469 | A1 * | 6/2003 | Karmon | 606/92 |
| 2003/0229340 | A1 * | 12/2003 | Sherry et al. | 606/27 |
| 2004/0102845 | A1 * | 5/2004 | Reynolds | 623/17.11 |
| 2005/0159737 | A1 * | 7/2005 | Kreindel | 606/32 |
| 2007/0016272 | A1 * | 1/2007 | Thompson et al. | 607/96 |
| 2007/0118112 | A1 * | 5/2007 | Kennedy, II | 606/45 |

(Continued)

*Primary Examiner* — Lynsey Crandall
*Assistant Examiner* — Manolis Pahakis (57) ABSTRACT

Disclosed are vertebroplasty methods that include cauterizing an inner cavity of a vertebra of a mammal, such as a human, and injecting bone cement into the vertebra. Systems and kits for performing such methods are also disclosed.

18 Claims, 4 Drawing Sheets

(56) References Cited

U.S. PATENT DOCUMENTS

| | | | |
|---|---|---|---|
| 2007/0118144 A1* | 5/2007 | Truckai et al. | 606/93 |
| 2007/0191858 A1* | 8/2007 | Truckai et al. | 606/92 |
| 2008/0021463 A1* | 1/2008 | Georgy | 606/61 |
| 2008/0269761 A1* | 10/2008 | Truckai et al. | 606/94 |
| 2011/0137317 A1* | 6/2011 | O'Halloran et al. | 606/92 |
| 2014/0128877 A1* | 5/2014 | O'Halloran et al. | 606/94 |

* cited by examiner

VERTEBRAL BODY NERVE AND VEIN CAUTERIZING SYSTEM AND METHOD

CROSS-REFERENCE TO RELATED APPLICATIONS

The present application is a continuation of U.S. patent application Ser. No. 12/605,836, entitled "Vertebral Body Nerve and Vein Cauterizing System and Method," filed on Oct. 26, 2009, now U.S. Pat. No. 8,282,628 the entire disclosure of which is incorporated herein by reference.

FIELD OF THE INVENTION

The present application is generally directed to vertebroplasty and kyphoplasty systems and methods that include cauterization, which include e.g., cauterization by heat and/or freezing (cryo-ablation) of an inner cavity of a vertebral body prior to insertion of bone cement (such as standard bone cements, bone growing agents, bone glue, etc.) into the cavity.

BACKGROUND OF THE INVENTION

Vertebroplasty is a medical procedure in which acrylic bone cement such as Polymethyl Methacrylate (PMMA) is percutaneously injected into a fractured vertebra to stabilize the vertebra. An osteoporotic fracture can cause extreme back pain along with other symptoms, such as decreased height and spinal deformity or a hunchback appearance. The main goal of vertebroplasty is to reduce pain caused by the fracture by stabilizing the bone.

The procedure, which typically involves the minimally invasive delivery of bone cement, such as PMMA, is typically used for a spine fracture caused by osteoporosis, a disease that causes weakening of the bones and can lead to fractures in the vertebral bodies. The procedure may offer early relief to older patients suffering osteoporotic compression fractures and refractory pain. Vertebroplasty may also be used to treat steroid-induced osteoporotic compression fractures, vertebral body hemangiomas and metastatic disease of the spine. If left untreated, fractures will continue to cause pain. Posterior displacement of the vertebral body can occur, which can cause pressure on nerves of the spinal cord and can lead to neurological deficit.

Vertebroplasty stabilizes or hardens the fracture, thus reducing the pain. In particular, increasing the rigidity and strength of the bone through the injection and subsequent hardening of PMMA cement reduces bone deformation and painful micro-motion at the fracture site. This is the consolidation effect.

Most patients experience pain relief within hours and are able to resume their daily activities within 48 hours. These procedures can even be performed with local anesthetic only for patients with severe lung disease who cannot tolerate sedatives well.

A problem may arise with vertebroplasty however, in that PMMA by-products may be sucked into blood and carried through micro veins in the cancellous bone to other regions of the body, which can cause inadvertent negative results, such as an embolism in the lungs (obstruction of one of the pulmonary arteries by an embolus).

SUMMARY OF THE INVENTION

Example embodiments are generally directed to vertebroplasty and kyphoplasty methods that include cauterization (by heat or freezing) of an inner cavity of a vertebral body prior to insertion of bone cement, bone growing agents, bone glue, etc. into the cavity. The methods herein may reduce or eliminate extravasation of bone cement, bone glue, etc. from the vertebral body into the body into the blood stream and/or are capable of reducing or stopping pain generated by sensitive nerve ending micro-motion.

Other embodiments are directed to kits or systems that include devices, components or ingredients for performing the methods herein.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF THE DRAWINGS

Non-limiting example embodiments described herein, with reference to the following accompanying Figures.

DETAILED DESCRIPTION

Generally provided herein are vertebroplasty and kyphoplasty methods that include cauterizing (e.g., by heat cauterization or by cryo-ablation) an inner cavity of a fractured vertebra of a mammal.

Also provided herein are systems and kits that include one or more ingredients or devices to be used in cauterizing or cryo-ablation of an inner cavity of a fractured vertebra in the vertebroplasty and/or kyphoplasty methods provided herein, and optionally including one or more ingredients typically used for known vertebroplasty and/or kyphoplasty methods.

The aspects, advantages and/or other features of example embodiments of the invention will become apparent in view of the following detailed description, taken in conjunction with the accompanying drawings. It should be apparent to those skilled in the art that the described embodiments of the present invention provided herein are merely exemplary and illustrative and not limiting. Numerous embodiments of modifications thereof are contemplated as falling within the scope of the present invention and equivalents thereto.

Unless otherwise noted, technical terms are used according to conventional usage. All patents and publications mentioned in this specification are indicative of the level of those skilled in the art to which the invention pertains. All publications, patent applications, patents, and other references mentioned herein are incorporated by reference in their entirety.

In describing example embodiments, specific terminology is employed for the sake of clarity. However, the embodiments are not intended to be limited to this specific terminology.

As used herein, "a" or "an" may mean one or more. As used herein, "another" may mean at least a second or more. Furthermore, unless otherwise required by context, singular terms include pluralities and plural terms include the singular.

Methods provided herein include vertebroplasty and kyphoplasty methods, which include cauterizing (e.g., heat cauterizing or cryo-ablation) an inner cavity of a fractured vertebra of a mammal; and thereafter inserting bone cement into the fractured vertebra of the mammal. The term "bone cement" is intended to encompass known and to be developed bone sealing, attaching and/or growing agents (including for example standard bone cements, such as PMMA, or other bone cements, bone growing agents, and/or bone glues), alone or in combination with one another, that may be used in vertebroplasty and/or kyphoplasty methods.

Cauterization may be performed using one or more methods or techniques that may include for example, heated fluid circulation, laser techniques (e.g., plasma laser), bi-polar/electric methods, using ultrasonic oscillating energy, microwave, cryo-ablation/cryogenic treatment or another other method that has the effect of being able to cauterize vessels and/or exposed nerve endings within a vertebral body prior to insertion of bone cement. According to exemplary embodiments, the heating/cauterization temperature may be between 56 and 100 degrees Celsius, which may achieve blood flow stagnation and dull the sensitivity of nerve endings. Initial heat increases blood flow and further heat coagulates blood cell flow. Heated fluid circulation may include for example, heat fluid delivery via contained vessel. In alternate embodiment, a flexible balloon, or similar member, may include an integrated electrical circuit or mesh therewith, similar to an electric blanket. The balloon may be inserted into a patient's bone, such as the vertebra, in a collapsed condition and can subsequently inflated or expanded to create a cavity or fill an existing cavity in the bone. The electrical mesh may be sandwiched between multiple layers of material and may be remotely electrical stimulated to heat up to cauterize at least a portion of the interior cavity of the bone, or vertebral body.

In embodiments in which the cauterization is cryo-ablation or cryogenic treatment, such terms include freezing a desired area of pathological tissue to destroy the area, for example, by inducing cold necroses at temperatures down to −196° C. Such freezing may be performed for example, using cryoinstruments (e.g., cryoprobes, cryoscalpels, cryoclamps, cryoneedles) that may be cooled for example using liquid nitrogen As indicated above, a desired result of cauterization/cryo-ablation is to prevent bone cement by-products from being sucked into blood and carried through microveins. Therefore, cauterization methods (whether by heating or cooling) that has a result of sealing such vessels to help prevent the extravasation of bone cement or other vertebroplasty product into the vessels, is encompassed by the present application.

An additional desired result of the present methods, which include cauterization or cryo-ablation, is to stop or reduce pain generated by sensitive nerve ending micro-motion. Hardening of bone cement reduces some of the painful micro-motion at the fracture site. Pain relief is thought to be achieved by locking of bone fragments. The present methods, which include cauterization or cryo-ablation of the vessels and exposed nerve endings, would destroy exposed nerve endings and even further reduce or even stop pain generated by the sensitive nerve ending micro-motion. Any cauterization, or other heating or cooling method that would result in such exposed nerve ending destruction, is intended to be encompassed by the present application.

Insertion or delivery of bone cement into the fractured vertebra of the mammal may include for example, injection of bone cement into a vertebral body. Injection may be percutaneous injection or other forms of injection.

The bone cement may include one or more types of bone cement or other filler, bone glue and/or bone growing agents used in vertebroplasty or kyphoplasty techniques. Non-limiting examples of bone cement that may be used may include acrylic cements, such as Polymethyl Methacrylate (PMMA) bone cement alone or as part of a composition with other bone cements or other ingredients.

According to non-limiting example embodiments, the mammal may be for example, a human.

Figure 1:
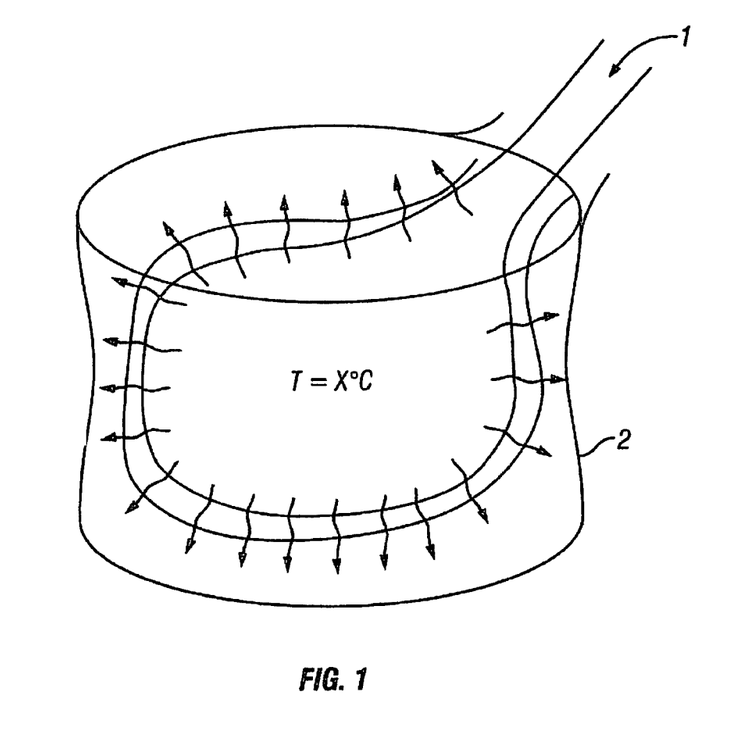
FIG. 1 depicts a vertebral body having heat input therein to cauterize an inner cavity of a fractured vertebra during a vertebroplasty procedure.

FIG. 1 depicts a vertebral body 2, which may have a heating element 1 input therein. The heating element 1 may include any heating or cooling element that results in cauterization or cryo-ablation of an inner cavity of a fractured vertebra according to the present methods. The arrows in FIG. 1 depict for example the direction of heat cauterizing or freezing an internal cavity of the vertebral body according to example embodiments.

Figure 2:
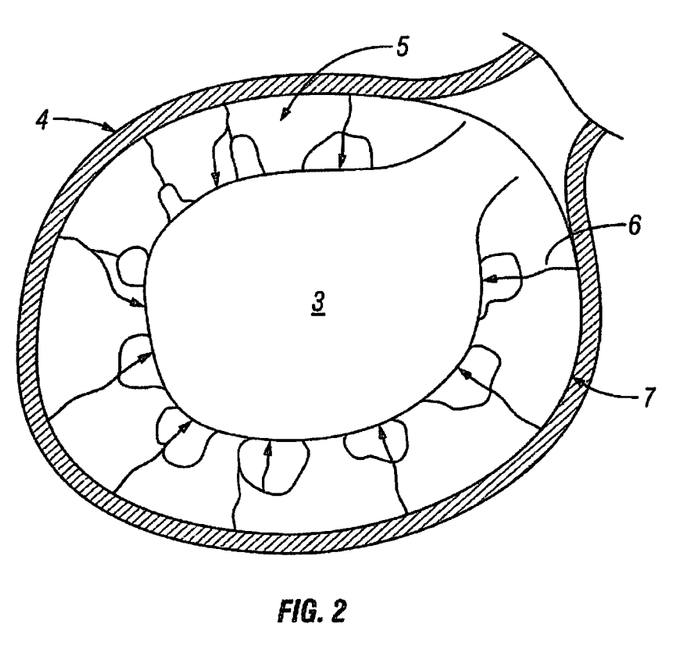
FIG. 2 depicts a vertebral body after cauterization of vessels and exposed nerve endings within the vertebral body.

FIG. 2 depicts a vertebral body 7, having at least one cavity 3 therein. The vertebral body may include a cortical shell 4. According to example embodiments, a heating element 1 (see FIG. 1) may be inserted into a cavity 3 of the vertebral body 7, to cauterize or cryoablate vessels and expose nerve endings 6 that may be exposed in the cavity 3 of the vertebral body 7. This cauterization, may help prevent or stop bone cement by-products from being sucked into blood in the vessels and carried through the microveins in the cancellous bone 5 to other regions of the body.

Figure 3:
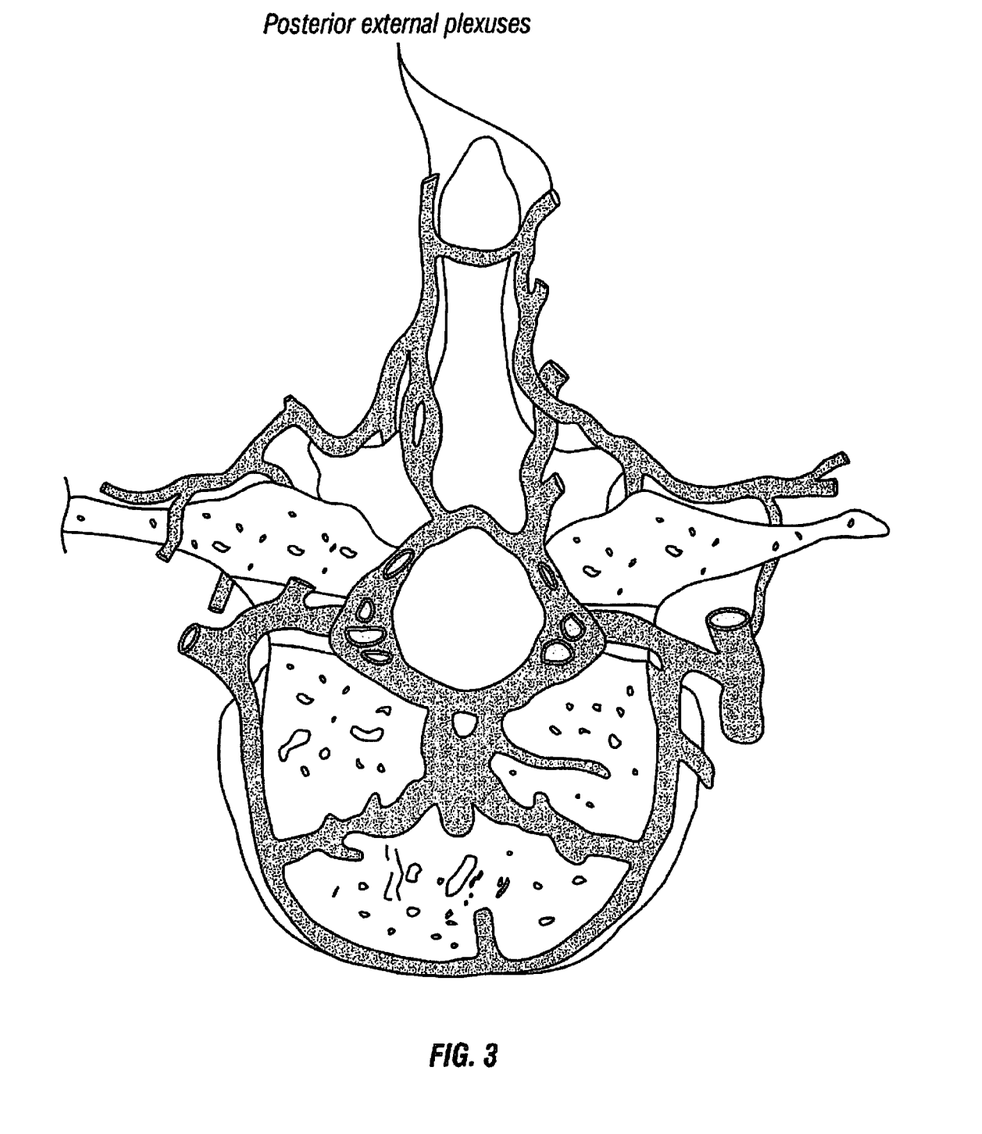
FIG. 3 is a transverse cross-sectional view of a vertebral body, showing the vertebral venous plexuses.

FIG. 3 depicts a top view of the blood vessels contained in one vertebral body.

Figure 4:
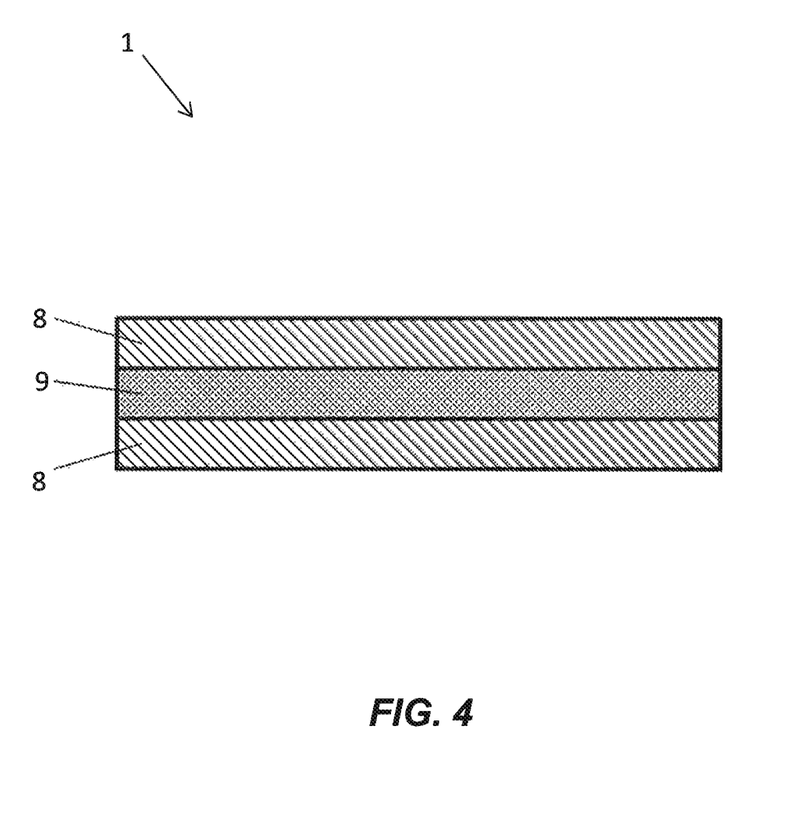
FIG. 4 depicts a portion of heating element with electrical mesh sandwiched between multiple layers of material.

FIG. 4 depicts a portion of heating element 1 with electrical mesh 9 sandwiched between multiple layers of material 8.

Further encompassed herein are vertebroplasty methods, which include creating a cavity in a fractured vertebra of a mammal; restoring body height of the fractured vertebra; cauterizing or cryo-ablating the inner cavity of the fractured vertebra; and inserting bone cement into the fractured vertebra. Such methods may further include containing the cement within the cavity, at least until the cement has an opportunity to harden within the cavity. These methods may include the cauterizing and cryo-ablation methods discussed throughout this application for example with respect to other embodiments. The cement may include for example, the bone cement discussed with respect to other embodiments herein.

A cavity may be created mechanically or through other bone tampering device, as in kyphoplasty techniques. An example method of creating a cavity may be by using Hydro-Cision® or by using other methods and/or tools known to those skilled in the art.

Height can be restored for example, through a collapsed end plate. Expansion may be by kyphoplasty balloon or other mechanical means to hold the endplates jacked up prior to cement or bone filler introduction.

According to non-limiting example embodiments, creating a cavity in a fractured vertebra, restoring vertebral body height, cauterizing or cryoablation of the inner cavity, and inserting bone cement into the cavity of the fractured vertebra may be performed by the use of a single endoscopic instrument that can perform all of these functions.

The inserting or filling of bone cement into a vertebral body may include for example, filling at least 50%, 60%, 70%, etc. of the cavity in the fractured vertebra with bone cement, and does not necessarily require complete filling of the vertebral body or a cavity therein with bone cement. The term is meant to encompass adding an amount of bone cement or other vertebroplasty or kyphoplasty filler to a vertebral body in accordance with medically indicated vertebroplasty or kyphoplasty techniques.

Also provided herein are kyphoplasty methods that may include placing a balloon into the fractured vertebra (which may be for example, a collapsed vertebra); cauterizing or cryo-ablating an inner cavity of a fractured vertebra of a mammal; and inserting bone cement, such as acrylic bone cement, into the fractured vertebra of the mammal. The insertion may include for example percutaneously injecting bone cement. These methods may include the cauterizing and/or cryo-ablation methods discussed throughout this application for example with respect to other embodiments. The bone cement may include the bone cement discussed with respect to other embodiments herein.

According to non-limiting example embodiments, cauterization may be performed after a cavity is created, either mechanically or by a balloon or other cavity creation method.

According to further non-limiting example embodiments, the balloon may be inflated after placement into the fractured vertebra.

According to non-limiting example embodiments, the cavity creation balloon in kyphoplasty methods could be the cauterization means, if the balloon is inflated for example with hot fluid.

Further non-limiting example embodiments may include insertion of a dual lumen balloon into a patient, bone tampering using the balloon to create a cavity in a vertebral body while cauterizing (e.g., by insertion of hot liquid into the balloon); inserting bone cement into a cavity created by the balloon; and removing the balloon. Bone cement may also be inserted into the cavity or into a second cavity or portion thereof, created after removal of the balloon.

Further provided herein are systems and kits for performing vertebroplasty or kyphoplasty provided herein. Such systems and kits may include for example, one or more cauterizing/cryo-ablation elements, which may include for example one or more components or ingredients that may be used for cauterization and/or cryo-ablation in the methods and techniques herein, such as laser devices, microwave components, fluid and/or heating devices for heated fluid circulation, cryo-tools, etc. . . . . The methods or kits herein may also include one or more components (e.g., injection needles, imaging devices, etc) and/or ingredients (e.g. bone cement) that may be used with traditional vertebroplasty or kyphoplasty techniques, as modified to include the cauterization/cryo-ablation of the present methods.

The following examples are provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

EXPERIMENTAL EXAMPLES

Example 1

In this example a vertebroplasty technique is performed on a patient in need thereof. The below method and that of Example 2, may be modified for example as discussed in Example 3 below to include a cauterization step in accordance with the present methods.

The below procedure is an example of an outpatient procedure, but it is contemplated that numerous modifications may be made to the technique depending for example, on the patient (age, weight, general health, etc), on the location in the patient of the vertebral body to be treated, and on the type and severity of the injury.

Outpatient Procedure

1. Patient is placed in a prone position with padding under the torso and the hips in slight flexion. The arms are positioned above the shoulder, pressure points are padded, and joints are gently flexed.

2. Patient receives local anesthetic (or sedative) until the area is numb. Using a posterior lateral approach, overlying skin, subcutaneous tissue and periosteum of T12 vertebra would be infiltrated with local anaesthetic.

3. The doctor inserts one or two needles through a small incision, and the needle is placed in the vertebral body under direct visualization using fluoroscopy. (Percutaneous injection). An 11 G bone biopsy needle (OPTIMED CEMENTO set, High Wycombe, UK), would be introduced into the centre of the T12 vertebral body via a unilateral left intercostovertebral route.

4. Acrylic bone cement (e.g., Polymethyl Methacrylate (PMMA)) is injected in the vertebral body under high pressure and constant fluoroscopic guidance. Once satisfactory placement of the needle is confirmed on fluoroscopy and CT, 4 ml of cement (PMMA) (OSTEOPAL® V Vertebroplasty; Biomet Merck, Altdorf, Switzerland) may be injected into the vertebral body, under continuous lateral fluoroscopic control.

5. Fluoroscopy and CT images may be used to show adequate filling of the cement in the anterior two-thirds of the vertebral body. The patient would be checked for leakage of cement.

6. Under careful fluoroscopic visualization, PMMA cement and sterile barium or tungsten powder opacifier is slowly injected into the vertebral body, diffusing throughout the intertrabecular marrow space. The procedure is usually repeated through the contralateral pedicle unless there is adequate cross-filling of the vertebral body by the initial injection. The total volume of injected cement ranges from four to 12 cc. The cement sets in less than one hour and should stabilize the vertebra by forming a hard internal "cast."

7. At the completion of the procedure the needle is removed and a single subcuticular stitch or a Steri-Strip is placed.

8. Following the procedure, the patient is instructed to lie flat in the supine position for one hour to allow the cement to harden. Observation in the hospital should be continued for at least one to two hours, at which point most patients will be able to stand and walk with minimal or no pain.

9. Before being discharged, patients should be assessed for relief of back pain, focal neurologic deficit, or new chest pain. Some patients may require nonsteroidal anti-inflammatory drugs (NSAIDs) for procedure-related discomfort. Pain relief is often immediate but may take up to 72 hours.

10. The radiologist should follow up with the patient by telephone or office visit at prescribed intervals to assess the response to treatment and the durability of the results.

Bone cements that may be used in the present methods may be provided for example, as two-component materials. For example, bone cements may consist of a powder (i.e., prepolymerized PMMA and or PMMA or MMA co-polymer beads and or amorphous powder, radio-opacifies, initiator) and a liquid (MMA monomer, stabilizer, inhibitor). When mixed these yield a dough-like cement that gradually hardens.

The two components are mixed and a free radical polymerization occurs of the monomer when the initiator is mixed with the accelerator. The bone cement viscosity changes over time from a runny liquid into a dough like state that can be safely applied and then finally hardens into solid hardened material. The set time can be tailored to help the physician safely apply the bone cement into the bone bed to treat osteoporotic compression fractures.

During the exothermic free-radical polymerization process the cement heats up while setting. This polymerization heat reaches temperatures of around 42-100° C. in the body. Thus, the hardened bone cement is a load sharing entity in the body not causing bone resorption. Surgeons can judge the curing of the PMMA bone cement by pressing their thumb on it.

Example 2

According to this example, a cauterization or cryocauterization step may be added for example, after the patient receives anesthesia (step 2, Example 1) and before injection or other insertion of bone cement (Step 4 in both Examples 1 and 3).

Cauterization/cryo-ablation takes place after any desired cavity has been created for example, with a balloon.

Example 3

In an example of a kyphoplasty procedure, the above steps of Example 1 are generally followed, with several modifications. The kyphoplasty procedure involves for example a modification to step 3. In particular, according to an example embodiment, kyphoplasty may involve a step 3A, which includes placement of a balloon into a collapsed vertebra, followed by injection of bone cement to stabilize the fracture. This procedure is more commonly performed in the hospital setting. It requires the use of slightly bigger needles than the vertebroplasty procedure, and therefore there is typically slightly more post-procedural pain.

Both procedures typically are very effective, reducing pain in almost 90% of well-selected patients.

Example 4

According to this example, a cauterization or cryocauterization step may be added for example, after the potential placement of a balloon (Step 3A of Example 3), and before injection or other insertion of bone cement (Step 4 in both Examples 1 and 3).

Cauterization/cryocauterization takes place after the cavity has been created for example, with a balloon. According to example embodiments, the kyphoplasty balloon could become the cauterizing agent when filled with hot fluid.

One exemplary cryo-ablation technique similar to known methods of cryo-ablation of a uterus wall could be used.

Although the invention has been described in example embodiments, those skilled in the art will appreciate that various modifications may be made without departing from the spirit and scope of the invention, and such modifications are therefore included herein. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

What is claimed is:

1. A method of treating a spine comprising:
    inserting a flexible balloon into an inner cavity of a vertebral body of a mammal;
    inflating the flexible balloon;
    sealing vessels and destroying exposed nerve endings in the inner cavity of the vertebral body by heating the flexible balloon while inflated, the flexible balloon including an electrical mesh sandwiched between multiple layers of material;
    removing the flexible balloon; and
    subsequent to the sealing and the removing steps, inserting bone cement into the inner cavity of the vertebral body of the mammal.

2. The method of claim 1, wherein sealing vessels comprises cauterizing the vertebral body of the mammal.

3. The method of claim 1, wherein the bone cement comprises PMMA.

4. The method of claim 1, wherein the bone cement is inserted to cover at least 50% of a cavity formed in the vertebral body.

5. A method of treating a spine comprising:
    inserting a flexible balloon including an electrical mesh sandwiched between multiple layers of material into a vertebral body of a mammal;
    inflating the flexible balloon;
    heating the flexible balloon such that an interior cavity of the vertebral body is heated to a temperature of between 56 and 100 degrees Celsius in order to destroy exposed nerve endings;
    removing the flexible balloon; and
    subsequent to the heating and the removing steps, inserting bone cement into the vertebral body cavity of the vertebral body of the mammal.

6. The method of claim 5, wherein the bone cement comprises PMMA.

7. The method of claim 5, wherein the bone cement comprises at least one ingredient selected from the group consisting of bone glue and bone filler.

8. The method of claim 5, further comprising restoring body height of the vertebral body.

9. The method of claim 5, wherein inserting bone cement into the vertebral body of the mammal is performed percutaneously.

10. A method of treating a spine comprising:
    creating a cavity in a vertebral body of a mammal;
    inserting a flexible balloon into the cavity;
    sealing vessels and destroying exposed nerve endings in the cavity of the vertebral body Of the mammal by deploying and heating the flexible balloon, wherein the flexible balloon includes an electrical mesh sandwiched between multiple layers of material into the vertebral body;
    removing the flexible balloon; and
    subsequent to the sealing and the removing steps, inserting bone cement into the cavity of the vertebral body of the mammal.

11. The method of claim 10, wherein creating the cavity is performed by a balloon.

12. The method of claim 10, wherein sealing the vessels comprises applying a cauterization treatment.

13. The method of claim 11, wherein the cauterization treatment comprises applying heat between 56 and 100 degrees.

14. The method of claim 10, wherein the material comprises bone growing agents.

15. The method of claim 10, wherein the material comprises bone glue.

16. The method of claim 1, wherein subsequent hardening of the bone cement reduces bone deformation and painful micro-motion.

17. The method of claim 1, wherein the bone cement consists of a powder selected from the group consisting of a pre-polymerized PMMA, PMMA, and MMA co-polymer beads mixed with a liquid selected from the group consisting of MMA monomer, stabilizer, and inhibitor.

18. The method of claim 1, wherein the electrical mesh is remotely stimulated to heat up the flexible balloon.

\* \* \* \* \*